United States Patent [19]

Woog

[11] Patent Number: 5,235,968
[45] Date of Patent: Aug. 17, 1993

[54] APPARATUS FOR THERAPEUTICALLY CARING FOR THE MOUTH AND THROAT

[75] Inventor: Philippe-Guy E. Woog, Geneva, Switzerland

[73] Assignee: LPA-Broxo S.A., Geneva, Switzerland

[21] Appl. No.: 827,453

[22] Filed: Jan. 29, 1992

[51] Int. Cl.⁵ .................................... A61H 9/00
[52] U.S. Cl. .............................. 128/66; 433/80
[58] Field of Search .............. 433/77, 79, 80, 88; 220/671; 128/66

[56] References Cited

U.S. PATENT DOCUMENTS

| Re. 27,274 | 1/1972 | Mattingly | 128/66 |
|---|---|---|---|
| 3,420,228 | 1/1969 | Kalbfeld | 128/66 |
| 3,495,587 | 2/1970 | Freedman | 128/66 |
| 3,545,645 | 12/1970 | Smith | 220/671 |
| 4,770,632 | 9/1988 | Ryder et al. | 433/80 |
| 4,830,032 | 5/1989 | Jousson | 132/323 |
| 4,880,382 | 11/1989 | Moret et al. | 229/449 |
| 4,907,744 | 3/1990 | Jousson . | |
| 4,989,590 | 2/1991 | Baum et al. | 128/66 |
| 5,029,576 | 7/1991 | Evans, Sr. | 433/80 |
| 5,062,795 | 11/1991 | Woog | 433/80 |

FOREIGN PATENT DOCUMENTS 0298910 1/1989 European Pat. Off. .............. 433/80

Primary Examiner—Cary E. O'Connor
Attorney, Agent, or Firm—Kane, Dalsimer, Sullivan, Kurucz, Levy and Eisele

[57] ABSTRACT

The apparatus is a dental hygiene device for therapeutically caring for the mouth and throat. The liquid reservoir can be turned upside down to encase the liquid driving mechanism and the nozzle for a compact storage position. The sidewalls of the reservoir is undulated so as to provide a convenient way to grip or engage the lid of the reservoir.

5 Claims, 11 Drawing Sheets

APPARATUS FOR THERAPEUTICALLY CARING FOR THE MOUTH AND THROAT

BACKGROUND OF THE INVENTION

1. Field of the Invention

This invention pertains to an apparatus for therapeutically caring for the mouth and throat. The apparatus includes a liquid reservoir which can be inverted when not in use. The liquid reservoir further comprises sidewalls having undulations which strengthen the reservoir, present an aesthetic appearance and allow the user to grip the lid easily when the reservoir is in its upright position.

2. Description of the Prior Art

Dental hygiene devices includes means for spraying the oral cavity are well-known. In particular, U.S. Pat. No. 5,062,795 entitled "Therapeutically Caring for the Mouth and Throat" issued on Nov. 5, 1991 to Woog, whose disclosure is incorporated herein by reference, discloses a method and apparatus for moisturizing and therapy of the mouth and throat. A nebulized fine pulsating spray of relatively small droplets is applied. The pressure and temperature of the spray are controlled to obtain optimum penetration. A liquid pulse generator and moisturizing break-up nozzle are employed by the apparatus of this reference.

The apparatus of this reference, however, does not provide a convenient way to reduce its size during storage. Additionally, the apparatus of this reference has a fixed reservoir, which may lead some users not to dispose of all liquid before putting the apparatus into storage.

OBJECTS AND SUMMARY OF INVENTION

It is therefore an object of this invention to provide an apparatus for dental hygiene which can be reduced in size for storage.

It is therefore a further object of this invention to provide an apparatus for dental hygiene with a liquid reservoir which can be removed for ease in cleaning.

It is therefore a final object of this invention to provide an apparatus for dental hygiene which includes a simple way for the user to remove the lid of the liquid reservoir regardless of where the hand is put.

These and other objects are attained by providing an apparatus for dental hygiene with a liquid reservoir which is in an upright position over the apparatus when in use. However, when the apparatus is to be stored, the reservoir is flipped so that the reservoir encases the apparatus.

Moreover, the walls of the reservoir are undulated. This provides not only strength to the walls but allows the user, when the reservoir is in its upright position, to grip anywhere the lid of the reservoir without undue effort.

BRIEF DESCRIPTION OF THE DRAWINGS

Further objects and advantages of the invention will become apparent from the following description and claims, and from the accompanying drawings, wherein:

DETAILED DESCRIPTION OF THE PREFERRED EMBODIMENT

Figure 1:
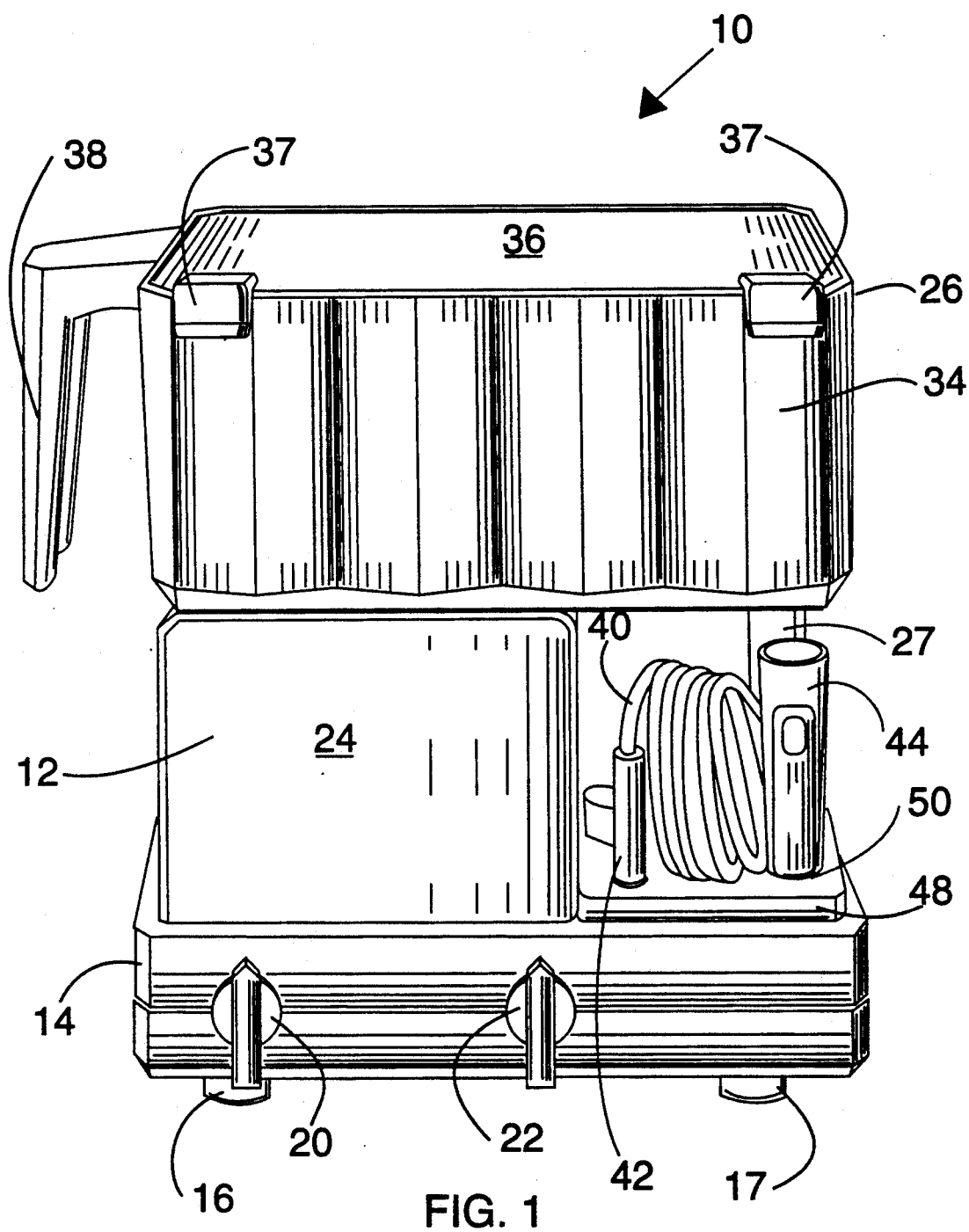
FIG. 1 is a front perspective view of the apparatus with the reservoir in an upright position.
Figure 8:
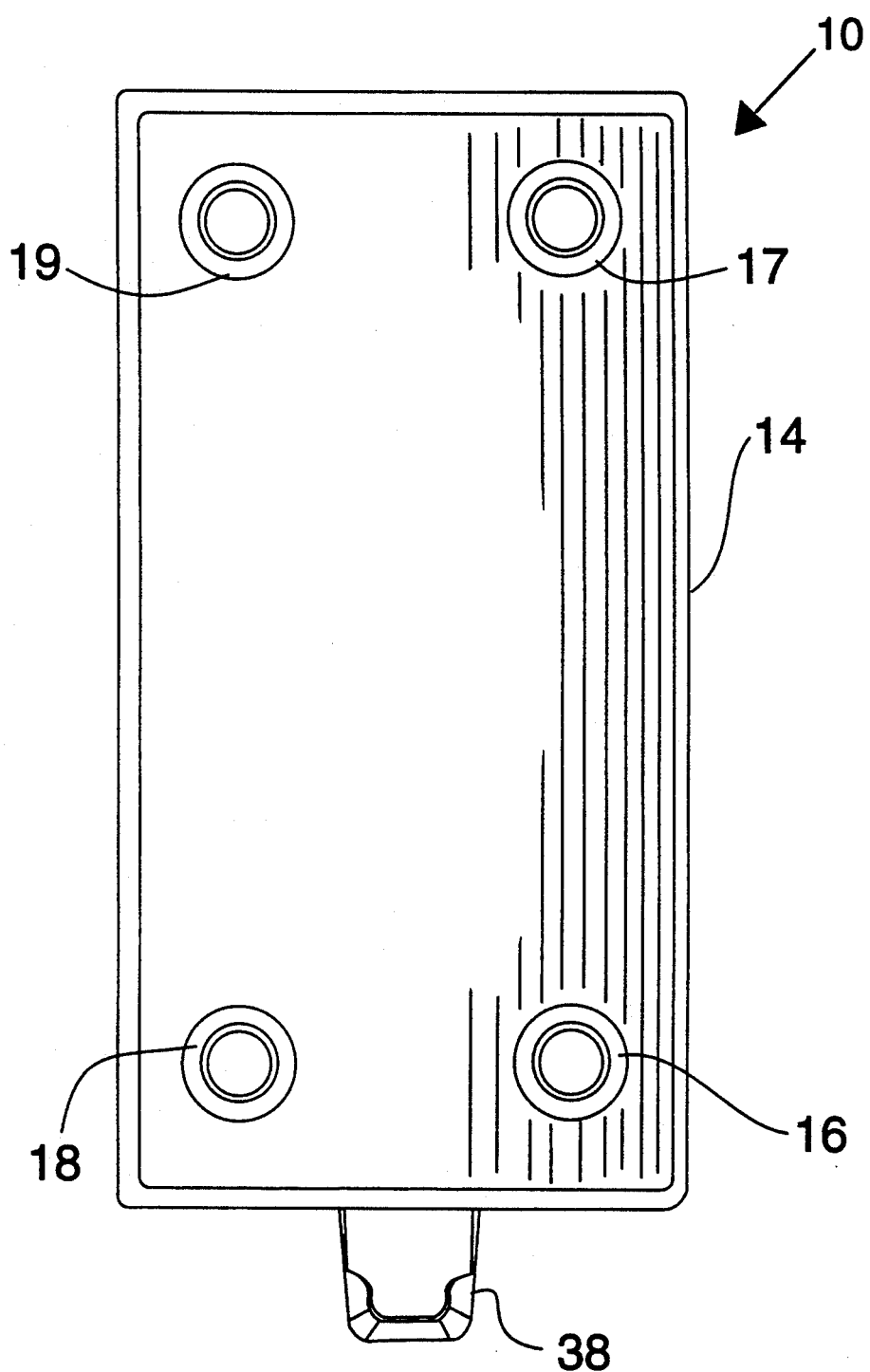
FIG. 8 is a bottom plan view of the apparatus.

Referring now to the drawings in detail wherein like numerals refer to like elements throughout the several views, a front perspective view of apparatus 10 is disclosed in FIG. 1. Base 12 includes rectangular pedestal 14 with four ground-engaging feet 16, 17, 18, 19 (see FIG. 8 for disclosure of feet 18 and 19). Pedestal 14 further includes two operational knobs 20, 22 which may include, as disclosed in U.S. Pat. No. 5,062,795, an on/off switch and a dial for setting the pressure of the liquid pulses or other combinations as are known to those skilled in the art. Knobs 20, 22 control the mechanism (not shown) encased in liquid pulse generator housing 24. The liquid pulse generator mechanism encased within housing 24 includes such apparatus as may be disclosed in U.S. Pat. No. 5,062,795.

Figure 7:
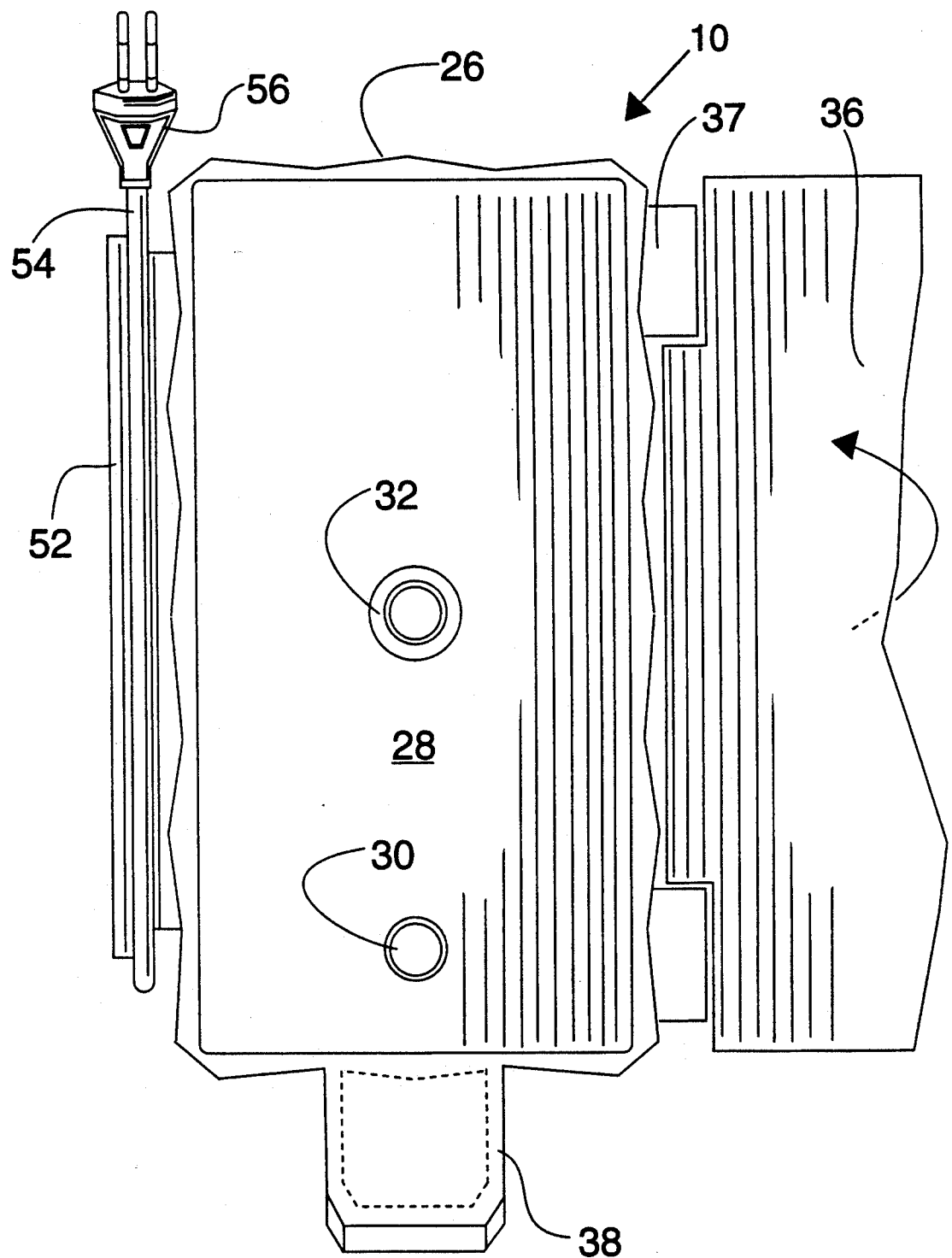
FIG. 7 is a top plan view of the reservoir of the apparatus.
Figure 9:
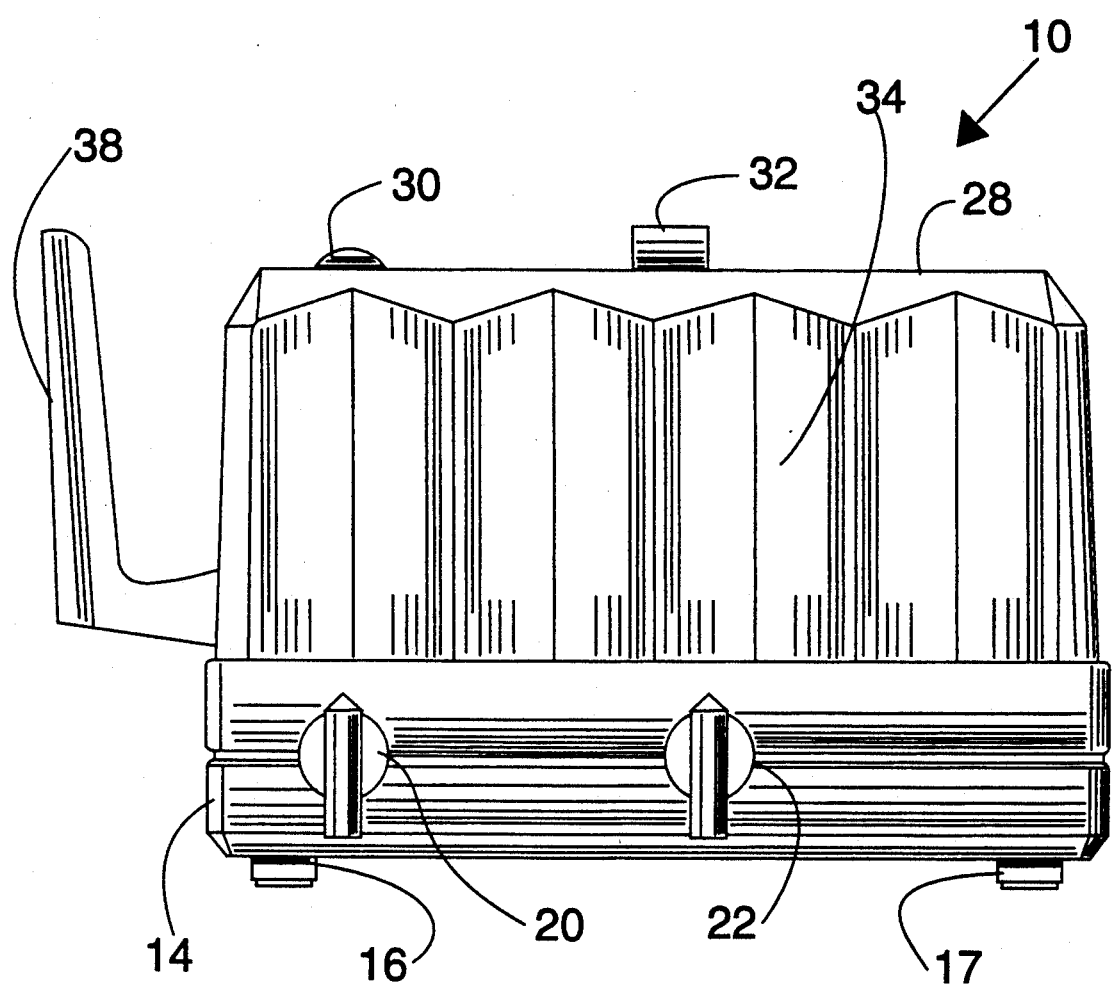
FIG. 9 is a front plan view of the apparatus with the reservoir in the inverted storage position.

Reservoir 26 is positioned above housing 24. As shown in FIGS. 7 and 9, the bottom 28 of reservoir 26 includes a partially hemispheric detent protrusion 30 and an aperture 32. When reservoir 26 is in its upright position, detent protrusion 30 engages a corresponding detent depression (not shown) on the top of housing 24 so as to position reservoir 26. Similarly, aperture 32 provides fluid communication from reservoir 26 to the mechanism within housing 24.

Support 27 rises from pedestal 14 to support reservoir 26.

Reservoir 26 further includes undulated sidewalls 34 which rise from bottom 28. The undulations of the sidewalls 34 are clearly illustrated in FIG. 7. Reservoir 26 is typically covered with lid 36 as is shown in FIGS. 1, 2, 3, 4, 5, and 6. Hinges 37 engage lid 36 to sidewalls 34. Although lid 36 is shown as one-piece, a two-piece lid (with the division between the lid pieces typically extending along a longitudinal axis of reservoir 26) with hinges on both the front and rear of reservoir 26 is possible.

Figure 11:
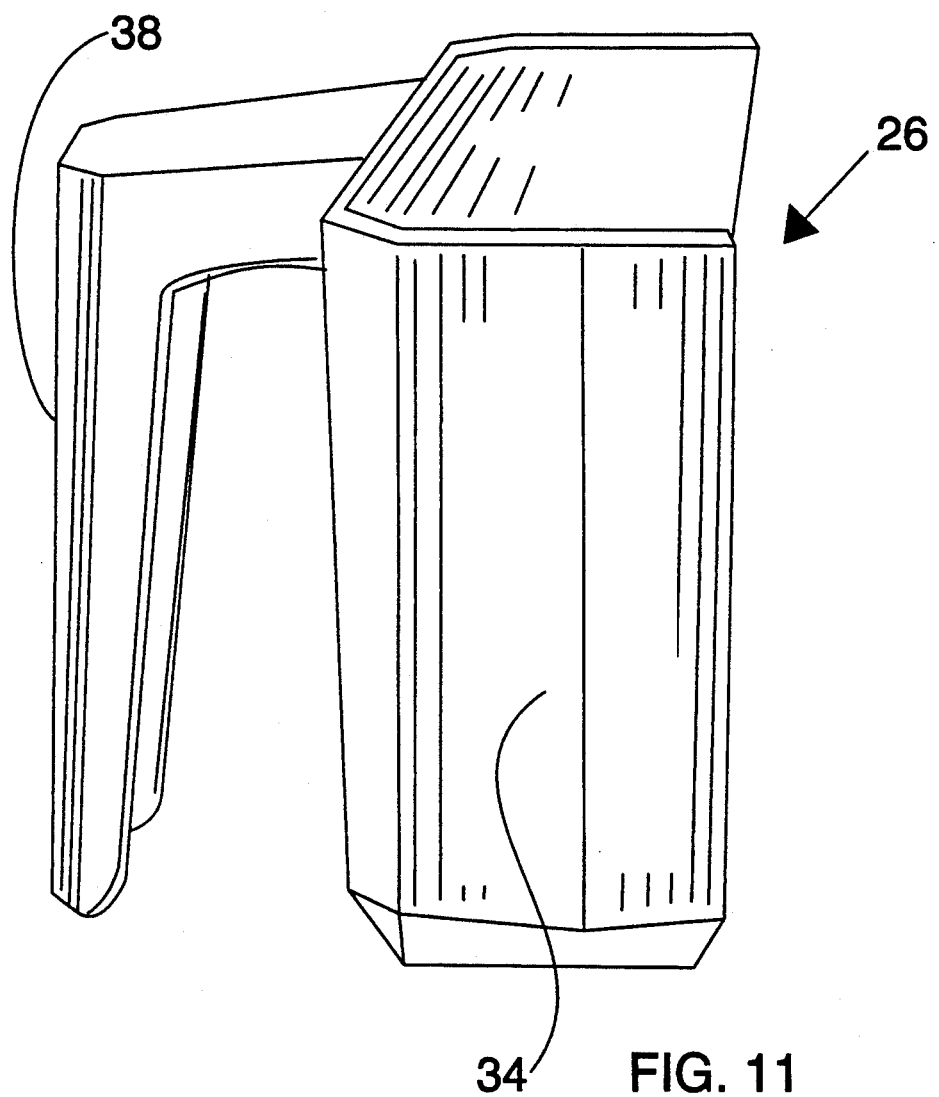
FIG. 11 is a front perspective fragmentary view of the handle of the reservoir of the apparatus.

Handle 38 (see FIG. 11) is attached to reservoir 26. Handle 38 allows the user to handle the reservoir 26 easily.

The mechanism encased in housing 24 draws water or other fluid from reservoir 26 through aperture 32 and drives the water through tubing 40 which is coaxial, in part, within post 42. Tubing 40 is in communication with handle 44. Handle 44 further engages any of nozzle attachments 46 (see FIGS. 2 and 4) such as are disclosed in the aforementioned U.S. Pat. No. 5,062,795.

Figure 2:
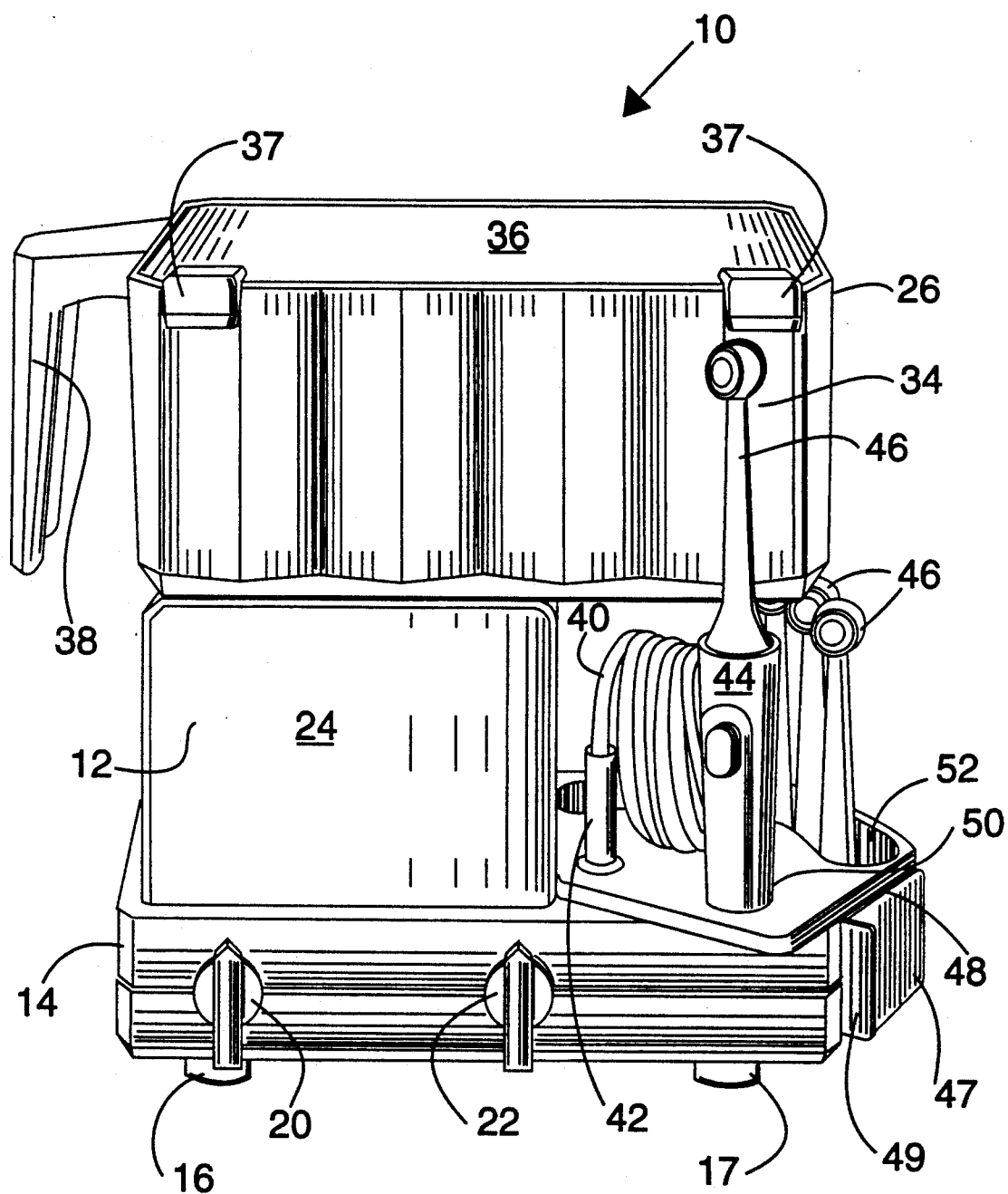
FIG. 2 is a front perspective view of the apparatus with the reservoir in an upright position and the accessory tray extended.
Figure 3:
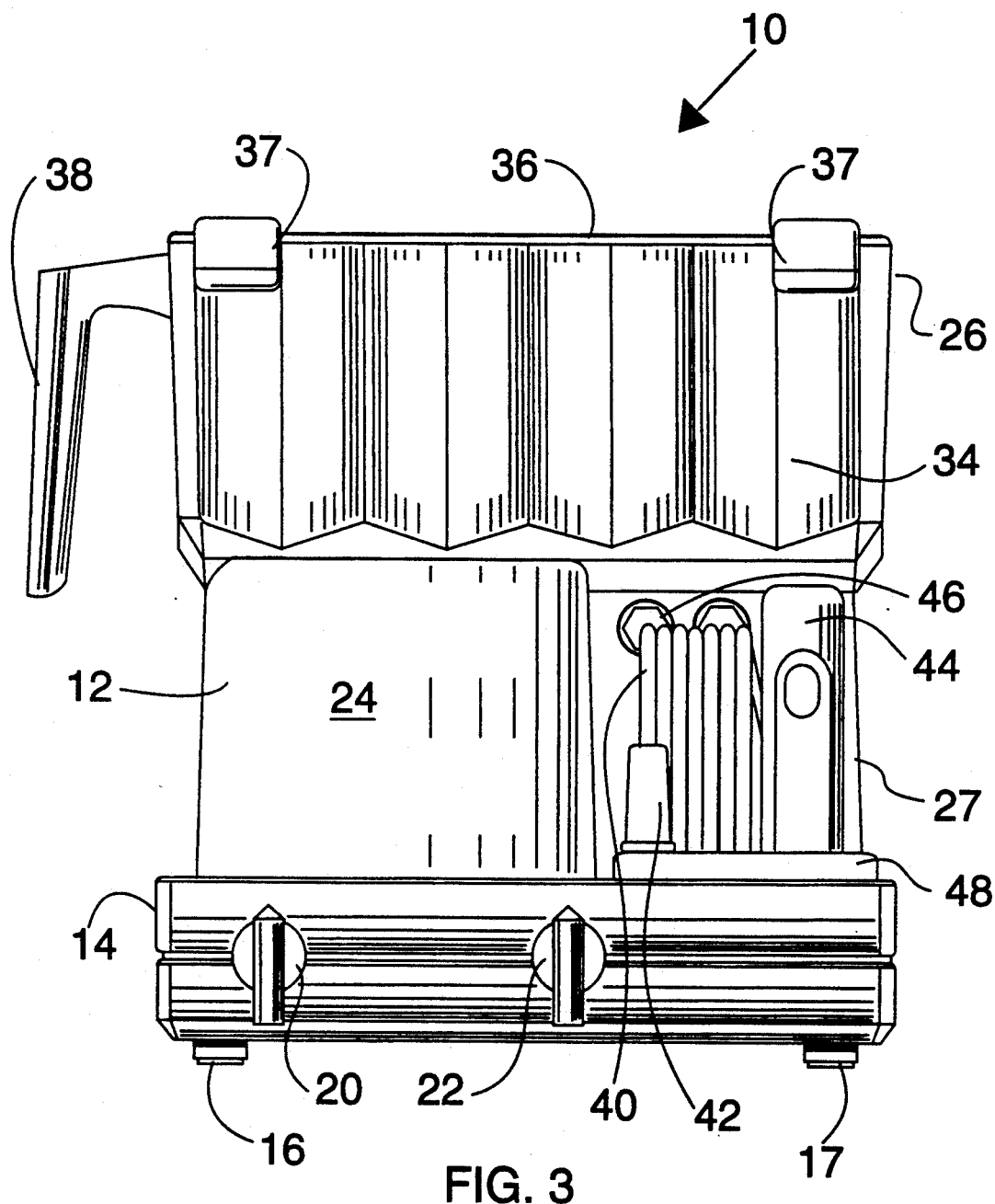
FIG. 3 is a front plan view of the apparatus with the reservoir in an upright position.
Figure 10:
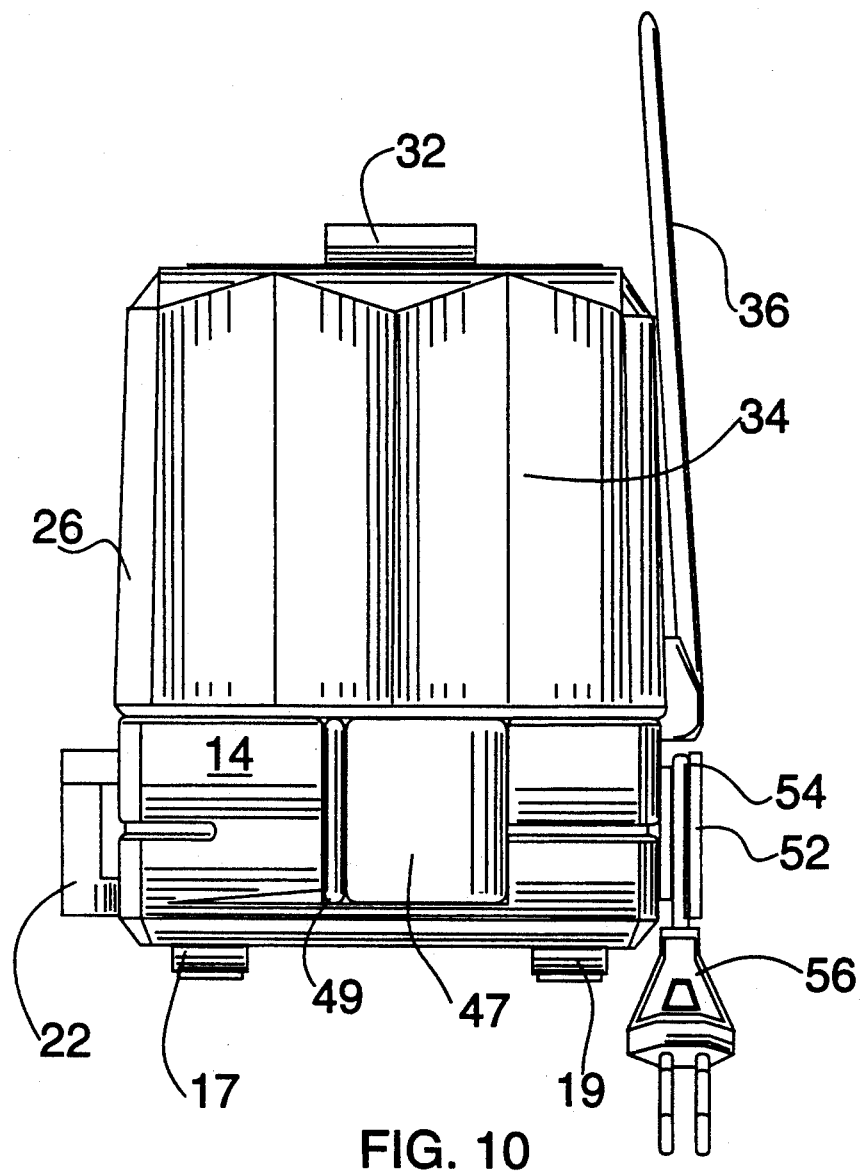
FIG. 10 is a side plan view of the apparatus with the reservoir in the inverted storage position.

Tray 48 pivots on post 42 as shown in FIGS. 1 and 2. Tray 48 includes aperture 50 to engage handle 44 and slot 52 which engages nozzle attachments 46. Integral handle 47 (shown on FIGS. 2, 5, and 10) which extends from tray 48 downwardly into pedestal 14 and includes outwardly extending lip 49 allows the user to easily rotate tray 48 into the position shown in FIG. 2.

Figure 4:
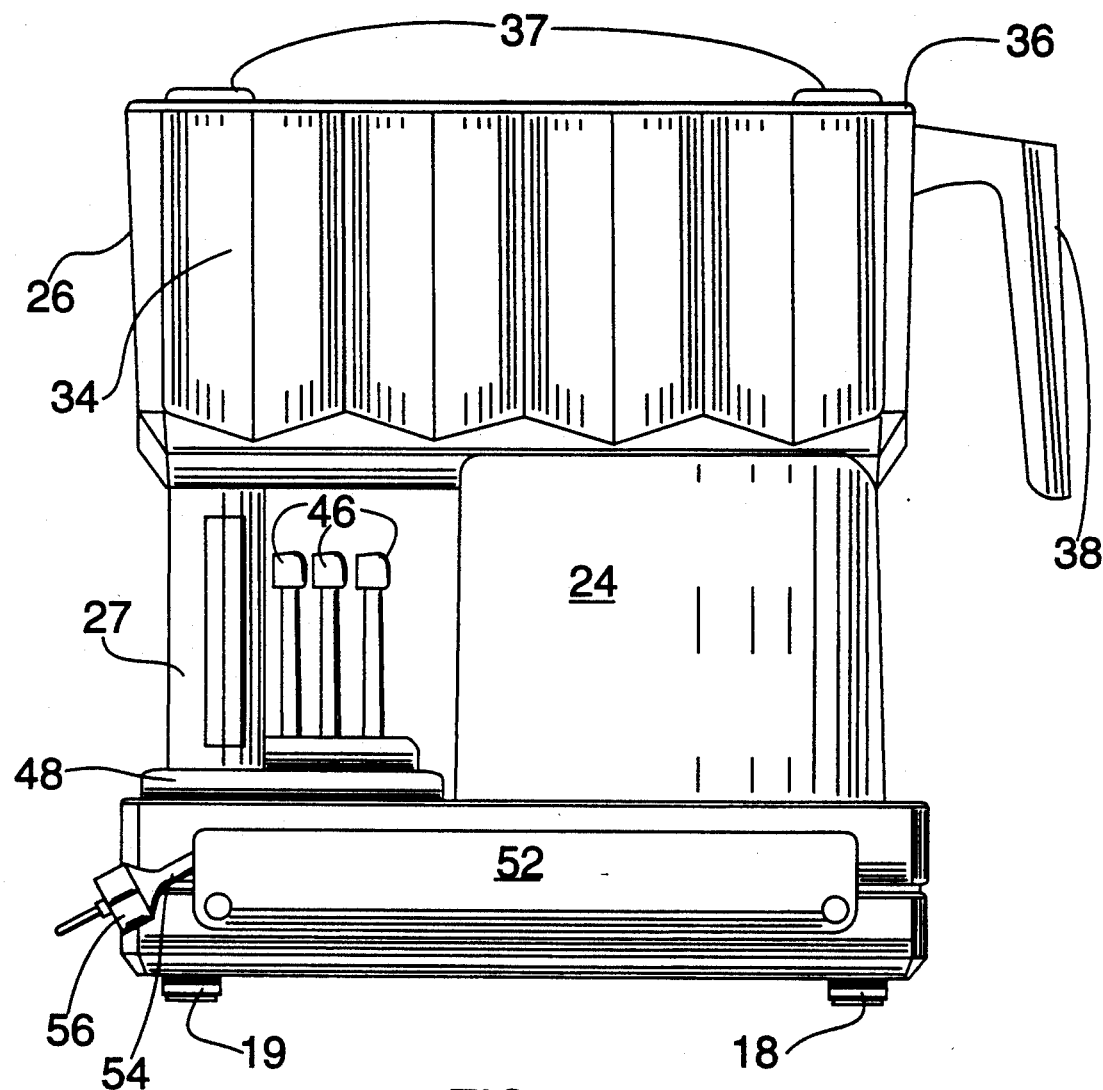
FIG. 4 is a rear plan view of the apparatus with the reservoir in an upright position.
Figure 5:
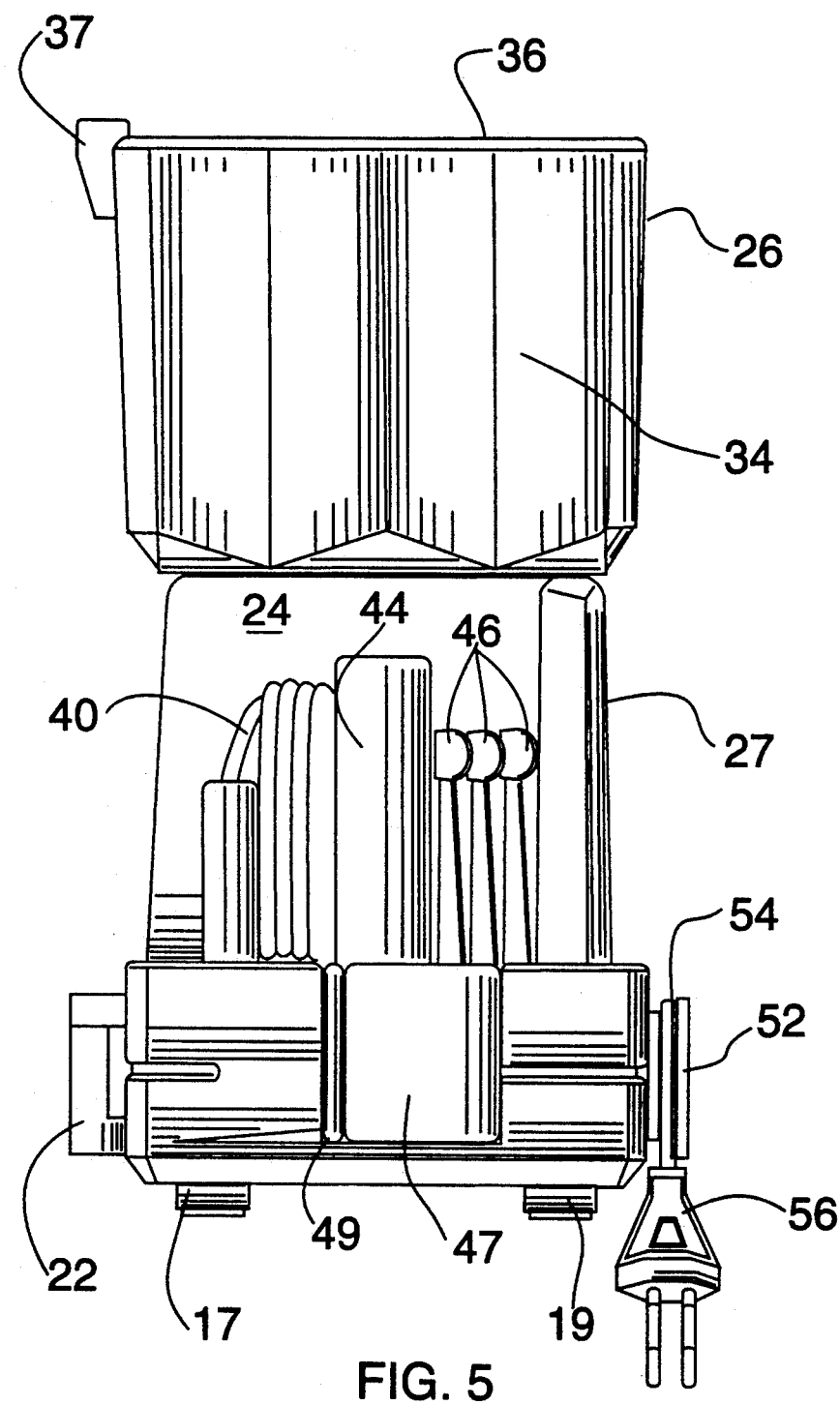
FIG. 5 is a right side plan view of the apparatus with the reservoir in an upright position.
Figure 6:
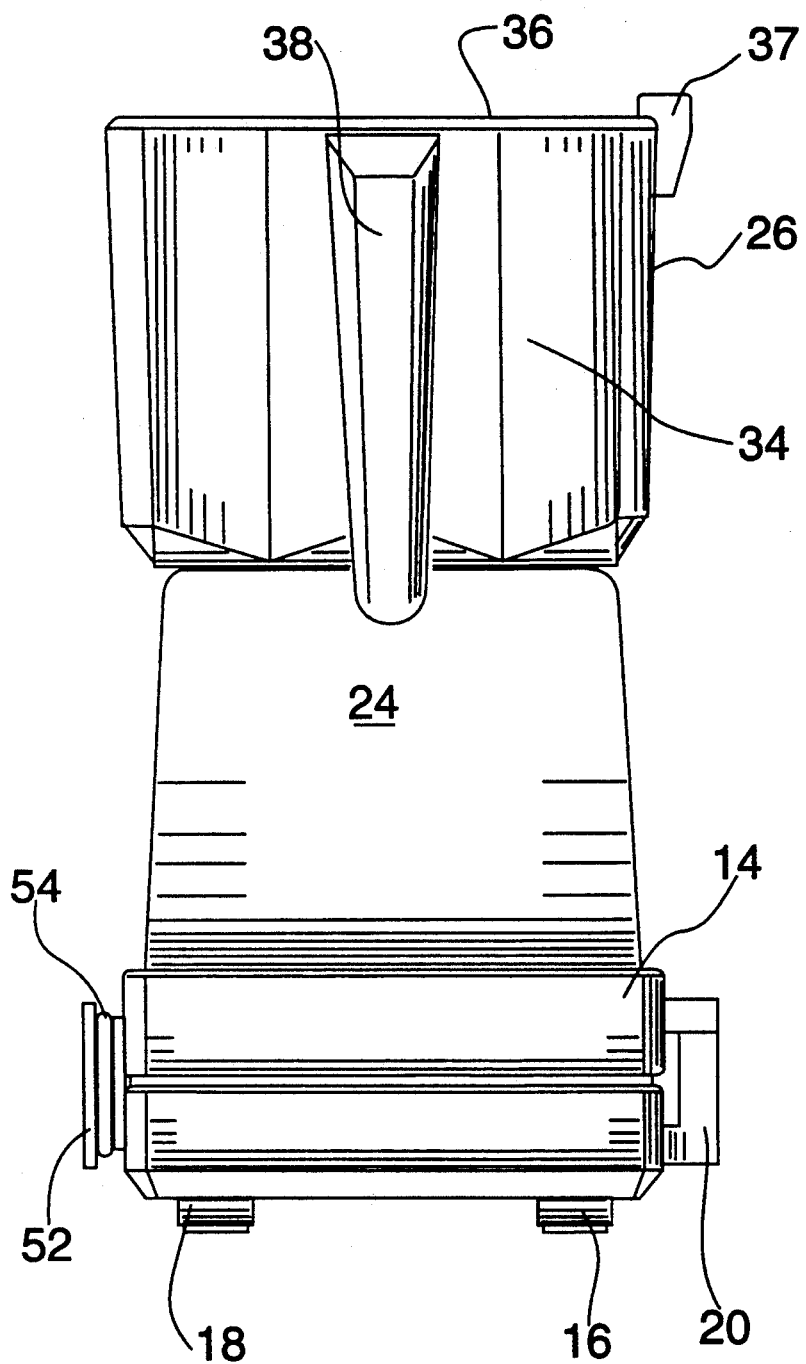
FIG. 6 is a left side plan view of the apparatus with the reservoir in an upright position.

As shown in FIG. 4, the rear of apparatus 10 includes flange 52 about which electric cord 54 (with electric socket 56) is wrapped. Electric cord 54, of course, is used to power the mechanism within housing 24.

To use apparatus 10, the user turns reservoir 26 to an upright position and fills reservoir 26 with water or an appropriate liquid. The user inserts plug 56 into an appropriate electrical socket. The user places his or her fingers within the undulations of sidewalls 34 to remove the lid 36, if necessary. The user further places a nozzle attachment 46 onto handle 44, and adjusts operational knobs 20, 22 so as to effect operation of apparatus 10 for dental hygiene.

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:

1. An apparatus for dental hygiene including:
   a nozzle means;
   a liquid driving means within a housing, said liquid driving means providing liquid to said nozzle means;
   a liquid reservoir comprising a bottom surface and upwardly extending undulated sidewalls for providing liquid to said liquid driving means when said liquid reservoir is in an upright position; and
   whereby when said liquid reservoir is emptied and turned upside down, said liquid reservoir encases said liquid driving means and said nozzle means.

2. The apparatus of claim 1 further including a lid for said reservoir wherein when said lid engages said reservoir, a portion of said lid extending from said undulated sidewalls thereby providing a gripping surface.

3. The apparatus of claim 2 wherein said liquid reservoir means further includes a handle.

4. The apparatus of claim 3 further including hinge means for attaching said lid to said sidewalls.

5. The apparatus of claim 1 wherein said liquid reservoir includes two longer sidewalls and two shorter sidewalls, as measured horizontally, wherein said longer sidewalls include substantially four undulations and said shorter sidewalls include substantially two undulations.

* * * * *